United States Patent
Voorhees et al.

(10) Patent No.: US 10,441,707 B2
(45) Date of Patent: Oct. 15, 2019

(54) SYSTEM AND METHOD FOR EXTRACORPOREAL TEMPERATURE CONTROL

(71) Applicant: Medivance Incorporated, Louisville, CO (US)

(72) Inventors: Marc E. Voorhees, Arvada, CO (US); Christopher Park, Oregonia, OH (US); Salvatore Privitera, Mason, OH (US)

(73) Assignee: MEDIVANCE INCORPORATED, Louisville, CO (US)

( * ) Notice: Subject to any disclaimer, the term of this patent is extended or adjusted under 35 U.S.C. 154(b) by 261 days.

(21) Appl. No.: 15/329,204

(22) PCT Filed: Aug. 5, 2015

(86) PCT No.: PCT/US2015/043855
§ 371 (c)(1),
(2) Date: Jan. 25, 2017

(87) PCT Pub. No.: WO2016/025268
PCT Pub. Date: Feb. 18, 2016

(65) Prior Publication Data
US 2017/0246374 A1    Aug. 31, 2017

Related U.S. Application Data

(60) Provisional application No. 62/037,437, filed on Aug. 14, 2014.

(51) Int. Cl.
*A61M 1/36*    (2006.01)
*A61F 7/00*    (2006.01)
(Continued)

(52) U.S. Cl.
CPC ........... *A61M 1/369* (2013.01); *A61F 7/0085* (2013.01); *A61F 7/12* (2013.01); *A61M 1/10* (2013.01);
(Continued)

(58) Field of Classification Search
CPC .................... A61M 1/10; A61M 1/369; A61M 2205/3368; A61M 25/0026; A61M 5/007; A61F 7/12
See application file for complete search history.

(56) References Cited

U.S. PATENT DOCUMENTS 3,064,649 A    10/1959  Fuson
4,894,164 A    1/1990   Polaschegg
(Continued)

FOREIGN PATENT DOCUMENTS

CA    2882654 A1    10/2007
EP    0322225 A2    6/1989
(Continued)

OTHER PUBLICATIONS

Bard Access Systems, Inc., Short-Term Dialysis Catheter Instructions for Use, Power-Trialysis Short-Term Dialysis Catheter, Mar. 2009, C.R. Bard Inc., Salt Lake City, Utah.
(Continued)

*Primary Examiner* — Leslie R Deak
(74) *Attorney, Agent, or Firm* — Marsh Fischmann & Breyfogle LLP; Thomas R. Marsh

(57) ABSTRACT

Improved systems and methods for extracorporeal blood temperature control and patient temperature control, e.g., for induced hypothermia and optional normothermia, may include or otherwise employ a heat exchanger for cooling/warming of a fluid, a thermal exchange module having fluidly isolated first and second volumes, and a fluid pump for circulating the fluid through the heat exchanger and the
(Continued)

first volume of the thermal exchange module. A blood pump may be provided for the flow of blood through the second volume of the thermal exchange module, and a first controller may be provided for providing output signals for use in operation of the heat exchanger to selectively control thermal exchange between the fluid circulated through the first volume of the thermal exchange module and the blood flowed through the second volume of the thermal exchange module, thereby providing for selective cooling/warming of the blood. A multi lumen catheter may be utilized for the flow of blood from a patient vascular system to the second volume of the thermal exchange module, and for flow of blood from the second volume of the thermal exchange module back to the patient vascular system. The circulated fluid may be optionally circulated through a patient contact pad(s) for contact cooling/warming, wherein patient cooling/warming may be provided in a first mode via blood cooling/warming in the thermal exchange module, and patient cooling/warming may be provided in a second mode via thermal exchange by the contact pad(s).

20 Claims, 4 Drawing Sheets

(51) Int. Cl.
*A61F 7/12* (2006.01)
*A61M 1/10* (2006.01)
*A61M 5/14* (2006.01)
*A61M 19/00* (2006.01)

(52) U.S. Cl.
CPC ....... *A61M 5/14* (2013.01); *A61F 2007/0056* (2013.01); *A61F 2007/0086* (2013.01); *A61F 2007/0096* (2013.01); *A61F 2007/126* (2013.01); *A61M 19/00* (2013.01); *A61M 2205/3355* (2013.01); *A61M 2205/3368* (2013.01)

(56) References Cited

U.S. PATENT DOCUMENTS

| | | | |
|---|---|---|---|
| 5,378,230 A | 1/1995 | Mahurkar | |
| 5,472,417 A | 12/1995 | Martin et al. | |
| 5,733,319 A | 3/1998 | Neilson et al. | |
| 6,375,674 B1 | 4/2002 | Carson | |
| 6,592,612 B1 | 7/2003 | Samson et al. | |
| 6,620,187 B2 | 9/2003 | Carson et al. | |
| 6,645,232 B2 | 11/2003 | Carson | |
| 6,699,267 B2 | 3/2004 | Voorhees et al. | |
| 7,241,307 B2 | 7/2007 | Lennox | |
| 7,827,815 B2 | 11/2010 | Carson et al. | |
| 8,092,415 B2 | 1/2012 | Moehle et al. | |
| 8,911,485 B2 * | 12/2014 | Brian | A61F 7/12 607/105 |
| 2003/0163183 A1 | 8/2003 | Carson | |
| 2005/0020958 A1 | 1/2005 | Paolini et al. | |
| 2005/0065583 A1 | 3/2005 | Voorhees et al. | |
| 2006/0177343 A1 | 8/2006 | Brian, III et al. | |
| 2009/0093748 A1 | 4/2009 | Patterson et al. | |
| 2009/0099629 A1 | 4/2009 | Carson et al. | |
| 2009/0131835 A1 | 5/2009 | Voorhees et al. | |
| 2010/0191165 A1 | 7/2010 | Appling et al. | |
| 2012/0029408 A1 | 2/2012 | Beaudin | |
| 2013/0324964 A1 | 12/2013 | Florescu | |

FOREIGN PATENT DOCUMENTS

| | | |
|---|---|---|
| WO | 199706840 A1 | 2/1997 |
| WO | 2006034877 A1 | 4/2006 |
| WO | 2006081288 A2 | 8/2006 |

OTHER PUBLICATIONS

Christoph Testori, et al., Rapid Induction of Mild Therapeutic Hypothermia by Extracorporeal Veno-Venous Blood Cooling in Humans, Resuscitation, 2013, vol. 84, pp. 1051-1055, Elsevier Ireland Ltd.
Bard Access Systems, Inc., Additional Instructions for Use of Power-Trialysis* Aphacurve* Short-Term Dialysis Catheter, Apr. 2012, C.R. Bard Inc., Salt Lake City, Utah.
Bard Access Systems, Inc., Flow Performance Guidelines for Bard Access Systems Power-Trialysis* Alphacurve* Short-Term Dialysis Catheter, Apr. 2012, C.R. Bard Inc., Salt Lake City, Utah.
Bard Access Systems, Inc., Power-Trialysis* Short-Term Dialysis Catheter Overview and Features, www.bardaccess.com/dial-power-trialysis.php, May 19, 2014, C.R. Bard Inc., Salt Lake City, Utah.
UCSF Department of Radiology & Biomedical Imaging, Vascular Access and Use of Central Lines and Ports in Adults, https://radiology.ucsf.edu/patient-care/patient-safety/contrast/iodinated/vascular-access-adults, May 15, 2014, The Regents of the University of California, San Francisco, California.

* cited by examiner

SYSTEM AND METHOD FOR EXTRACORPOREAL TEMPERATURE CONTROL

RELATED APPLICATIONS

This application claims priority to U.S. Patent Application No. 62/037,437, filed Aug. 14, 2014, entitled "SYSTEM AND METHOD FOR EXTRACORPOREAL TEMPERATURE CONTROL," which application is incorporated herein by reference in its entirety.

FIELD OF THE INVENTION

The present invention relates to systems and methods for use in extracorporeal blood temperature control and patient temperature control, and in particular, for therapeutic patient temperature cooling to induce hypothermia and optionally patient warming to achieve normothermia.

BACKGROUND OF THE INVENTION

There are a number of medical conditions for which systemic cooling is an effective therapy. For example, rapid systemic cooling of stroke, head-trauma, cardiac arrest, and myocardial infarction patients has significant therapeutic benefits.

In that regard, stroke is a major cause of neurological disability, but research has established that even though a stroke victim's brain cells may lose their ability to function during the stroke, they do not necessarily die quickly. Brain damage resulting from a stroke may take hours to reach a maximum level. Neurological damage may be limited and the stroke victim's outcome improved if a cooling neuroprotectant therapy is applied during that timeframe.

Similar possibilities exist with victims of trauma, such as may result from vehicle crashes, falls, and the like. Such trauma may impart brain injury through mechanisms that have overlap with elements in the genesis of neurologic damage in stroke victims. Delayed secondary injury at the cellular level after the initial head trauma event is recognized as a major contributing factor to the ultimate tissue loss that occurs after brain injury.

Further, corresponding possibilities exist with cardiac arrest and myocardial infarction patients. Again, rapid cooling of such patients may limit neurological damage. In addition, rapid cooling may provide cardio protection. Further in that regard, rapid heart cooling of myocardial arrest patients prior to reperfusion procedures (e.g., carotid stenting) may significantly reduce reperfusion-related injuries.

Additionally, patients having a neurological disease may often have accompanying fever. Cooling such patients has been recently proposed to yield therapeutic benefits, but may entail cooling over an extended period of time.

Various approaches have been developed for applying cooling therapy. In one non-invasive approach, a contact pad may be placed on a patient's torso and a cooled fluid, such as cooled water or air, circulated through the pad. Thermal energy is then exchanged between the patient and the circulated fluid to cool the patient. Other proposed approaches provide for esophageal cooling or invasive, intravascular cooling of a patient.

SUMMARY OF THE INVENTION

In relation to effective patient temperature control, it is desirable to provide a procedure that can be readily initiated, and that provides for rapid systemic cooling of patients to induce hypothermia. Further, it is desirable to provide for controlled and maintainable patient cooling. Also, in some applications, it is desirable to provide for patient cooling over an extended time period, while reducing undesirable, attendant conditions (e.g., extended use of heparin, extended vascular access location exposure to infection, etc.). Additionally, for many applications it is desirable to provide for patient rewarming (e.g., after induced hypothermia) to achieve normothermia in a controlled manner.

In view of the foregoing, improved systems and methods are provided herein for extracorporeal blood temperature control and patient temperature control, and in particular, for therapeutic patient temperature cooling to induce hypothermia and optionally for patient warming to achieve normothermia.

In one aspect, an embodiment of a system for extracorporeal blood temperature control includes a heat exchanger for at least cooling fluid (e.g., water), a thermal exchange module having a first volume and a second volume isolated from one another, and a fluid pump for circulating the fluid through the heat exchanger and the first volume of the thermal exchange module. In various embodiments, the heat exchanger may comprise one or a plurality of components for cooling and optionally warming the circulated fluid.

Optionally, the fluid pump may be provided so that operation of the fluid pump establishes a negative pressure within the first volume of the thermal exchange module, thereby reducing the risk of fluid flow from the first volume in to the second volume of the thermal exchange module in the event of a breach in the isolation therebetween. For example, the fluid pump may be provided so that the circulated fluid is circulated first through the heat exchanger and second through the second volume of thermal exchange module, wherein the fluid pump effectively draws the circulated fluid through the second volume at the thermal exchange module. In one approach, an inlet port of the fluid pump may be fluidly interconnected to an outlet port of the first volume of the thermal exchange module, and an outlet port of the thermal exchange module may be fluidly interconnected to a reservoir of the heat exchanger that is fluidly interconnected to an outlet port of the fluid pump, wherein upon operation of the fluid pump fluid is drawn from the reservoir and through the first volume of the thermal exchange module to the inlet port of the fluid pump.

The embodiment may further include a blood pump (e.g., a peristaltic pump) for flowing blood through a first blood flow line, the second volume of the thermal exchange module, and a second blood flow line. Optionally, the blood pump may be disposed upstream of the second volume of the thermal exchange module, wherein the blood pump pumps the blood through the thermal exchange module and second blood flow line at a positive pressure. In that regard, the blood pump may be provided so that blood is drawn through a first portion of the first blood flow line (i.e., upstream of the blood pump) at a negative pressure, and so that blood is flowed through a second portion of the first blood flow line (i.e., downstream of the blood pump) at a positive pressure.

Further, the embodiment may include a first controller for providing output signals for use in operation of at least the heat exchanger, and optionally, the first fluid pump, so as to selectively control thermal exchange within the thermal exchange module between the fluid circulated through the first volume of the thermal exchange module and the blood flowed through the second volume of the thermal exchange module and thereby selectively provide for at least cooling of the blood. In turn, selective patient cooling may be realized.

In some embodiments the output signals may control the heat exchanger in relation to on/off time cycle control (e.g., duty cycle) and/or in relation to the magnitude of thermal exchange provided (i.e., thermal exchange with circulated fluid) per unit time of operation. Further, the output signals may control the fluid pump in relation to on/off time cycle control (e.g., duty cycle) and/or in relation to the speed of pump operation.

In some implementations, the embodiment may include at least a first fluid temperature sensor for sensing a temperature of the circulated fluid and providing a first fluid temperature signal indicative thereof. Further, in some embodiments, the first controller may be provided to receive a patient temperature signal indicative of a sensed patient temperature. For example, a patient temperature signal may be provided by a patient temperature sensor that is utilized to sense a core body temperature of a patient. In addition, a blood temperature sensor may be included for sensing a temperature of the blood flowed through the second volume of the thermal exchange module and providing a blood temperature signal indicative thereof. By way of example, the blood temperature sensor may be disposed to sense the temperature of the blood flowed through the second volume of the thermal exchange module within the second volume of the thermal exchange module.

The first controller may be provided to utilize the first fluid temperature signal alone, or together with the patient temperature signal and/or the blood temperature signal, to generate the output signals to selectively control the thermal exchange between the circulated fluid and the blood. In some implementations, the first controller may be adapted to provide an output signal for use in operation of the blood pump. For example, such output signal may be employed to initiate operation of the blood pump and/or to terminate operation of the blood pump. In one approach, the controller may be provided to utilize the blood temperature signal to determine whether the sensed blood temperature is greater than a predetermined magnitude, in which case, the controller may provide an output signal to terminate operation of the blood pump.

In some arrangements, a multi-lumen catheter may be included for fluid interconnection to the first and second blood flow lines so as to receive blood from a patient vascular system for passage through the second volume of the thermal exchange module and to return the blood flowed through the second volume of the thermal exchange module to the patient vascular system. The use of a multi-lumen catheter advantageously provides for single catheter positioning into a patient vascular system, thereby simplifying the initiation of patient thermotherapy procedures. In that regard, the multi-lumen catheter may comprise a cannula portion having at least a first port and a second port, a first lumen fluidly interconnected to the first port and having an end fluidly interconnectable to the first blood flow line, and a second lumen, fluidly interconnected to the second port, and having an end fluidly interconnectable to the second blood flow line. The second port may be disposed distal to the first port, wherein upon positioning of the multi-lumen catheter in a vein of a patient (e.g., the femoral vein or subclavian vein of the patient), the first port is positioned upstream of the downstream second port.

In contemplated embodiments, the thermal exchange module, the blood pump, the first and second blood flow lines, and the multi-lumen catheter may be adapted to selectively provide for a blood flow rate within a range of about 5 ml/min to 500 ml/min through the second volume of the thermal exchange module. In some implementations, the noted components may be provided to provide for blood flow through the second volume of the thermal exchange module at a blood flow rate within a range of about 50 ml/min to 300 ml/min. Additionally, the system may be provided to circulate fluid through the first volume of the thermal exchange module at a rate that is at least about 5 times greater than, and preferably at least about 10 times greater than the blood flow rate through the second volume of the thermal exchange module.

Further, in various embodiments, the thermal exchange module may be provided to have a heat exchange performance factor $N>0.8$ across a blood flow rate range of about 50 ml/min to about 300 ml/min, wherein:

$$N = \frac{T_{bo} - T_{bi}}{T_{cfi} - T_{bi}};$$

and, $T_{bo}$=temperature of blood flowing out of thermal exchange module;

$T_{bi}$=temperature of blood flowing in to thermal exchange module; and, $T_{cfi}$=temperature of circulated fluid flowing in to thermal exchange module.

In conjunction with noted parameters, the system may provide for rapid blood cooling to realize a patient cooling rate of at least 4° C./hr, and in some applications at least 8° C./hr. Such rapid cooling facilitates rapid organ cooling, thereby enhancing neuro protection and cardio protection, e.g., prior to reperfusion by carotid stenting or other similar reperfusion procedures.

In one approach, the catheter portion of the multi-lumen catheter may further comprise a third port, wherein the multi-lumen catheter includes a third lumen, fluidly interconnected to the third port, having an end selectively, fluidly interconnectable to an optional component. In some implementations, the optional component may comprise a fluid source, e.g., a source of a fluid that comprises one of an anticoagulant (e.g., heparin), an anti-shivering agent (e.g., meperidine), a contrast media (e.g., a radio opaque iodine or barium compound), or a cooled fluid (e.g., a cooled saline solution). When the optional component includes a fluid source, the optional component may further comprise a device (e.g., a pump and/or syringe) for positive displacement of the fluid from the fluid source and into the third lumen for passage to a patient vascular system. In another implementation, the optional component may comprise a blood pressure sensor for sensing blood pressure at the third port that the multi-lumen catheter and for providing a pressure output signal indicative of the sensed blood pressure.

In some embodiments, the controller (e.g., a microprocessor) may comprise a programmable control module for establishing and storing control data (e.g., storing on a computer readable medium) in relation to a plurality of different temperature control phases (e.g., non-overlapping phases which may be successive) during which a temperature of the circulated fluid is controlled differently. In that regard, the programmable control module may comprise control logic for utilizing the control data to provide output signals to the heat exchanger and/or the fluid pump and/or the blood pump, wherein the temperature of the circulated fluid is controlled in a predetermined manner for each of the plurality of different temperature control phases.

The control data may provide cooling control data for use by the control logic to provide an output signal to the heat exchanger to provide for cooling of the circulated fluid in at least one of the plurality of temperature control phases. Further, the control data may comprise warming control data for use by the control logic to provide an output signal to the heat exchanger to provide for warming of the circulated fluid in at least another one of the plurality temperature control phases.

In some embodiments, the control data for a first phase of the plurality of different temperature control phases may be established to comprise at least one of a target patient temperature and/or a target blood temperature and/or a duration measure. Further, the control data for a second phase of the plurality of different temperature control phases may be established to comprise at least one of a target patient temperature and/or a target blood temperature and/or a duration measure. Additionally, the control data for a third phase of the plurality of different temperature control phases may be established to comprise at least one of a target patient temperature and/or a target blood temperature and/or a duration measure.

In one approach, the control data for a first phase of the plurality of different control phases may be established so that, during the first phase, the circulated fluid may be cooled to cool the blood circulated through the thermal exchange module so that the patient reaches an established target patient temperature (e.g., corresponding with induced hypothermia). For such purposes, the controller may utilize a patient temperature signal as referenced above to determine whether or not and when a patient has reached the established target patient temperature (e.g., by comparison of the corresponding patient temperature to the established target patient temperature) and to provide output signals to the heat exchanger and/or fluid pump responsive thereto. In one implementation, the circulated fluid may be cooled at a predetermined rate (e.g., a predetermined maximum rate) to cool a patient to the established target patient temperature as rapidly as possible (e.g., within predetermined system limits).

Optionally, the control data for the first phase of the plurality of different control phases may further comprise an established duration measure, wherein once the established target patient temperature is reached the patient is maintained at the established target patient temperature for any remaining portion of the established duration measure. Alternatively, the control data for a second phase of the plurality of different control phases may be established so that, during the second phase, the circulated fluid may be maintained at a temperature so that, via thermal exchange with the blood circulated through the thermal exchange module, the patient is maintained at the established target patient temperature for an established duration of the second phase. Again, for such purposes, the controller may utilize a patient temperature signal, as referenced above (e.g., to compare the corresponding patient temperature to the established target patient temperature) and to provide output signals to the heat exchanger and/or fluid pump responsive thereto.

In further conjunction with the described approach, the control data for an additional phase after the first phase (e.g., a second phase or a third phase of the plurality of different control phases) may be established so that, during such phase, the circulated fluid may be warmed (e.g., at a predetermined rate) to warm the blood circulated through the thermal exchange module so that the patient reaches another established target patient temperature (e.g., corresponding with normothermia), and optionally, so that once such another established target patient temperature is reached, the patient is maintained at the another established target patient temperature for any remaining balance of an established duration of the additional phase or until the thermotherapy procedure is manually terminated by a user. For such purposes, the controller may again utilize a patient temperature signal, as referenced above (e.g., to compare the corresponding patient temperature to the another established target patient temperature), and to provide output signals to the heat exchanger and/or fluid pump responsive thereto.

In some implementations, the controller may further comprise a user interface for receiving user input and providing user control signals, wherein the control logic of the programmable processor control module utilizes the user control signals together with the control data to provide the output signals. The user interface may be further provided to establish and modify the control data stored by the programmable control module.

In some arrangements, the programmable control module may be operable to store at least two protocols comprising corresponding, different control data. In turn, the user interface may be employable by user to select either of the two protocols for use by the programmable control module in generating the output signals.

Optionally, the user interface may be provided to include a graphic display to visually present a plot of a target patient temperature adjustment rate that is based on the stored control data for a plurality of different temperature control phases. Further, the graphic display may be operable to display a plot of a sensed patient temperature (e.g., as sensed by the patient temperature sensor) in corresponding time relation to the plot of the target patient temperature adjustment rate. Additionally, the graphic display may be operable to display a plot of a sensed temperature of the circulated fluid (as sensed by the first fluid temperature sensor) and a sensed temperature of the blood flowed through the second volume of the thermal exchange module (as sensed by the blood temperature sensor) in corresponding time relation to the plot of the target patient temperature adjustment rate.

In another aspect, an embodiment of a multi-mode system for extracorporeal patient temperature control includes a fluid conditioning assembly, a blood thermal exchange assembly, fluidly inter-connectable to the fluid conditioning assembly for patient temperature control in a first mode of operation, and at least a first patient contact pad, fluidly interconnectable to the fluid circulation assembly for patient temperature control in a second mode of operation. The fluid conditioning assembly may cool, optionally warm, and circulate a fluid that is provided to the blood thermal exchange assembly in the first mode of operation and that is provided to the first patient contact pad in the second mode of operation.

In one approach, the fluid conditioning assembly may include a heat exchanger for cooling and optionally warming the fluid, a fluid pump for circulating the fluid through the heat exchanger, and a controller for providing output signals for use in operation of the heat exchanger, and for use in operation of the fluid pump in some embodiments, to selectively control cooling and optional warming of the circulated fluid. Further, the thermal exchange assembly may include a thermal exchange module having a first volume and a second volume fluidly isolated from one another. In the first mode of operation, the first volume is fluidly interconnected with the fluid circulation assembly so that the fluid pump circulates the circulated fluid through the first volume.

The thermal exchange assembly may further include a blood pump for flowing blood from and to a patient through a second volume of the thermal exchange module. In turn, the output signals provided by the controller may selectively control the thermal exchange between the fluid circulated through the first volume of the thermal exchange module and the blood flow through the second volume of the thermal exchange module, thereby providing for patient cooling and optional warming. The controller may receive a first fluid temperature signal and a patient temperature signal for use in generating the output signals, as described above.

In the second mode of operation, the fluid pump circulates fluid through the heat exchanger and the at least one patient contact pad. In the later regard, the patient contact pad(s) may be provided for direct skin contact with a patient (e.g., for thermal exchange across an adhesive surface of the pad). Output signals provided by the controller may selectively control thermal exchange between the at least one patient contact pad and patient, thereby providing patient cooling and optional warming. For such purposes, the controller may again receive a first fluid temperature signal and patient temperature signal for use in generating the output signals provided to the heat exchanger and/or the fluid pump.

In some implementations, the blood thermal exchange assembly may include a multi-lumen catheter fluidly interconnectable or interconnected to a first blood flow line to flow blood to the second volume of the thermal exchange module from a patient vascular system. Additionally, the multi-lumen catheter may be fluidly interconnectable or interconnected to a second blood flow line to flow blood from the second volume of the thermal exchange module to a patient vascular system.

In one approach, the multi-lumen catheter may include a cannula portion having at least a first port and a second port. Additionally, the multi-lumen catheter may include a first lumen, fluidly interconnected to the first port and having an end fluidly interconnectable or interconnected to the first blood flow line. Additionally, the multi-lumen catheter may include a second lumen fluidly inter-connected to the second port and having an end fluidly interconnectable or interconnected to the second blood flow line. Optionally, the first port of the cannula portion may be located proximal to the second port of the cannula portion. In turn, upon vascular positioning of the multi-lumen catheter (e.g., in the femoral vein or subclavian vein of a patient), the second port may be positioned "downstream" of the first port, wherein blood is removed through the "upstream" first port and cooled blood is returned through the "downstream" second port.

In contemplated applications, the multi-mode embodiment may incorporate a controller that comprises a programmable control module for establishing and storing control data in relation to a plurality to different temperature control phases, as described above. The programmable control module may comprise control logic for utilizing the control data to provide output signals to the heat exchanger and/or the fluid pump and/or the blood pump, wherein the temperature of the circulated fluid may be controlled in a predetermined manner for each of the plurality of different temperature control phases, and wherein at least a portion or all of at least one of the plurality of different temperature control phases may be completed in the first mode of operation and another portion or all of another one of the plurality of different temperature control phases may be completed in the second mode of operation.

In one approach, the first mode of operation (i.e., during which circulated fluid and blood are circulated through the thermal exchange module) may be employed during at least a first phase of the plurality of different temperature control phases. For example, in the first phase, the first mode of operation may be employed for all or at least a portion thereof, wherein the blood circulated through the thermal exchange module may be rapidly cooled to cool the patient to an established target patient temperature (e.g., comprising the corresponding first phase control data). Then, in any remaining portion of the first phase and/or in a second phase during which the patient may be maintained at the established target patient temperature for an established duration (e.g., comprising the corresponding first phase or second phase control data), the second mode of operation may be employed. Further, in an additional phase after the first phase (e.g., a second phase or third phase) during which the patient may be warmed (e.g., at a predetermined rate) to another established target patient temperature (e.g., comprising the corresponding second phase or third phase control data) and optionally maintained at such temperature for any remaining balance of an established duration (e.g., comprising the corresponding second phase or third phase control data), the second mode of operation may be employed.

In a further aspect, an embodiment of a method for extracorporeal blood temperature control may include operating a fluid pump to circulate a fluid through a heat exchanger and a first volume of a thermal exchange module, and flowing blood through a second volume of the heat exchange module that is fluidly isolated from the first volume. Additionally, the method may include controlling the heat exchanger to selectively control thermal exchange between the fluid circulated through the first volume of the thermal exchange module and the blood flowing through the second volume of the thermal exchange module to provide for the selective cooling, and optionally warming, of the blood.

In one method implementation, the operating step may provide for the establishment of a negative pressure within the first volume of the thermal exchange module. By way of example, the operating step may include drawing the fluid through the first volume of the thermal exchange module. In one approach, the fluid pump may be disposed so that the inlet thereto is downstream of an outlet of the first volume of the thermal exchange module, wherein operation of the fluid pump establishes the negative pressure in the first volume of the thermal exchange module so as to draw the fluid therethrough.

Optionally, the flowing step of the method embodiment may include receiving the blood from a first lumen of a multi-lumen catheter into the second volume of the thermal exchange module, and returning the blood from the second volume of the thermal exchange module to a second lumen of the multi-lumen catheter. As may be appreciated, such arrangements may entail positioning a cannula portion of the multi-lumen catheter in to a patient's vascular system (e.g., a patient vein), wherein blood is received and returned through the cannula portion.

In some implementations, the flowing step may provide for the flow of blood through the second volume of the thermal exchange module at a blood flow rate within a range of about 50 ml/min to about 300 ml/min. Further, the operating step may provide for circulation of the fluid through the first volume of the thermal exchange module at a rate that is at least about 5 times greater than the blood flow rate through the second volume of the thermal exchange module. Additionally, the thermal exchange module may be provided to have a heat exchange performance factor N>0.8 across a blood flow rate range of about 50 ml/min to about 300 ml/min, as described above.

In some implementations, the controlling step may include utilizing a first temperature signal indicative of the temperature of the circulated fluid. Additionally, the controlling step may further include utilizing a patient temperature signal indicative of a temperature of a patient. Further, the controlling step may include utilizing a blood temperature signal indicative of a temperature of the blood. In conjunction with this described embodiment, it should be appreciated that the programmable control module features described herein may be utilized for patient temperature control in relation to a plurality of different temperature control phases.

In an additional aspect, an embodiment of a multi-mode method for extracorporeal patient temperature control may include the steps of circulating a fluid through a first volume of a thermal exchange module in a first-mode of operation, and flowing blood from a patient through a second volume of the heat exchange module for return to the patient in the first mode of operation, wherein the blood is cooled and optionally heated by the fluid for patient cooling and optional warming. The method embodiment may further include the step of passing the fluid through at least one patient contact pad in contact with the patient in a second mode of operation for patient cooling and optional warming. In this regard, patient cooling and optional warming may be advantageously realized via vascular thermal exchange and via patient contact pad thermal exchange.

In some multi-mode method embodiments, the circulating and flowing steps may be carried out in a first period of patient temperature control, and the passing step may be carried out in a second period of patient temperature control. The second period of patient temperature control may be carried out after completion of the first period of patient temperature control. By way of example, in some implementations, the circulating and flowing steps may be carried out to rapidly cool a patient via blood cooling in a first period, wherein patient organs are rapidly cooled during the first period. Then, at the initiation of or during the second period of patient cooling, the circulating and flowing steps may be terminated, wherein further patient cooling during the second period may be achieved via one or more patient contact pads. In that regard, after the patient has been cooled to a first patient target temperature (e.g., corresponding with induced hypothermia), the first period may be terminated and the second period initiated, wherein the patient may be maintained at the first patient target temperature for at least a portion of the second period. As may be appreciated, upon termination of the first period, the multi-lumen catheter may be removed from the patient's vein. Further, during at least a portion of the second period, the circulated fluid may be heated, wherein the patient contact pad(s) may be utilized for warming of the patient. For example, during the second period the patient may be warmed to a second patient target temperature (e.g., corresponding with normothermia) and optionally maintained at the second patient target signal until the completion of thermotherapy.

In some implementations, the circulating step may include operating a fluid pump to circulate the fluid through a heat exchanger and the first volume of the thermal exchange module, wherein the fluid is cooled and optionally warmed by a heat exchanger. Additionally, the passing step may include operating the fluid pump to circulate the fluid through a heat exchanger and the at least one patient contact pad, wherein the fluid is cooled and/or warmed by the heat exchanger. In conjunction with the noted steps, operation of the fluid pump in the circulating step may establish a negative pressure within the first volume of the thermal exchange module, and operation of the fluid pump in the passing step may establish a negative pressure within the at least one patient contact pad.

The method may further comprise the step of controlling the heat exchanger during the circulating and flowing steps to selectively control thermal exchange between the fluid circulated through the first volume of the thermal exchange module and blood flowing through the second volume of the thermal exchange module, thereby controlling thermal exchange with the patient. In addition, the controlling step may include controlling the heat exchanger during the passing step to selectively control thermal exchange between the fluid circulated through the patient contact pad(s) and the patient. Further, the controlling step may include utilizing a first temperature signal indicative of a temperature of the circulated fluid, and utilizing a patient temperature signal indicative of the temperature of a patient. Further, the controlling step may include utilizing a blood temperature signal indicative of the temperature of the blood flowing through the second volume of the thermal exchange module.

As may be appreciated, the features of the various systems and methods described herein, as well as embodiments thereof, may be used together in various combinations. In turn, numerous additional features and advantages of the present invention will become apparent to those skilled in the art upon consideration of the embodiment descriptions provided hereinbelow.

DETAILED DESCRIPTION

Figure 1:
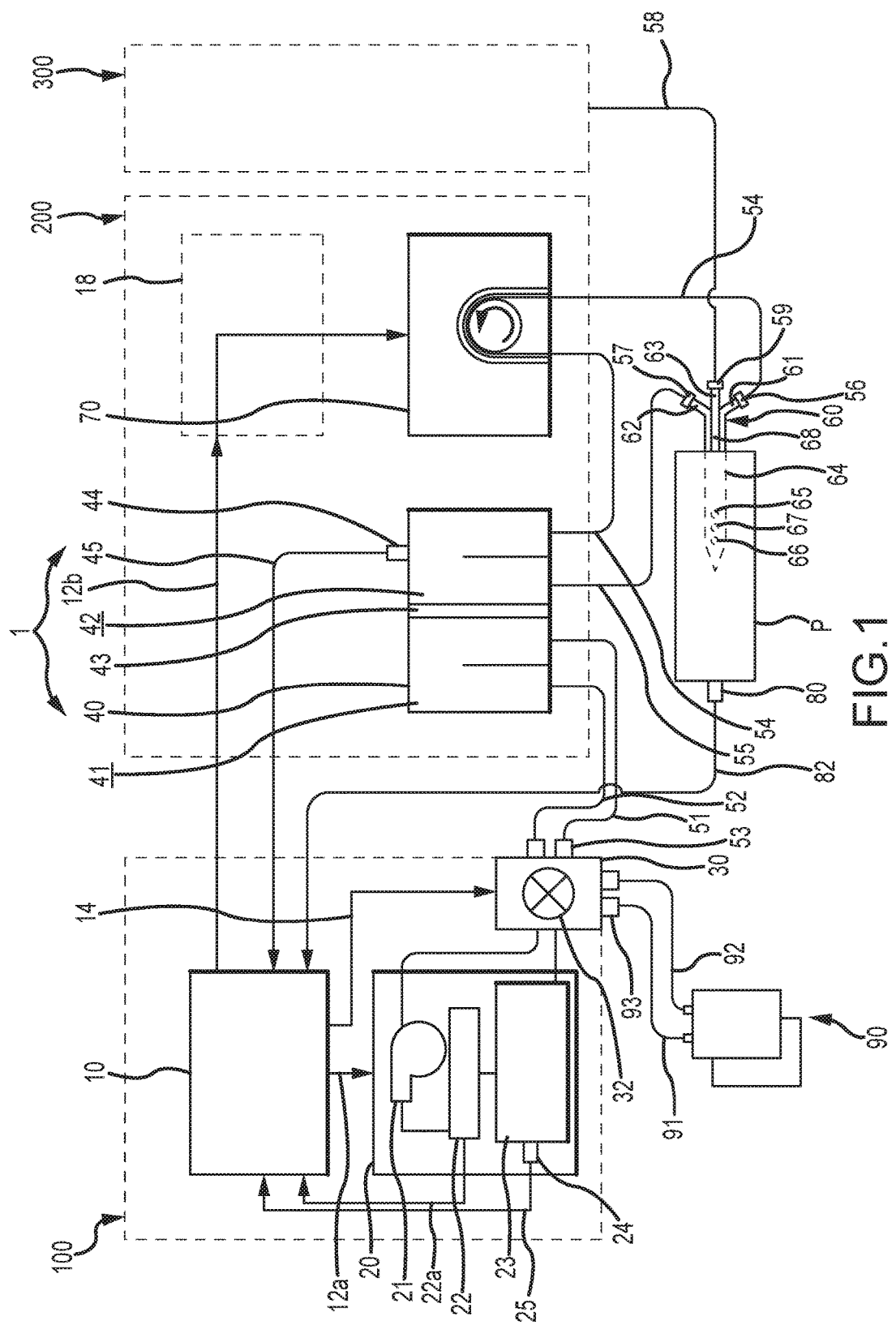
FIG. 1 is a schematic illustration of one embodiment of a system for extracorporeal blood temperature control and patient temperature control.

FIG. 1 schematically illustrates one embodiment of a system 1 for extracorporeal blood temperature control and patient temperature control. The system 1 includes a controller 10 for providing output signals for use in the operation of a fluid conditioning assembly 20 so as to cool, optionally warm, and circulate fluid through a thermal exchange module 40. In turn, the fluid conditioning assembly may include a fluid pump 21 for circulating the fluid to a heat exchanger 23 for passage to a fluid coupling interface 30. In one implementation, the controller 10, fluid conditioning assembly 20, and fluid coupling interface 30 may be supportably interconnected to a first support structure 100.

A first fluid circulation line 51 (e.g., a length of flexible tubing) and a second fluid circulation line 52 (e.g., a length of flexible tubing) may each be fluidly interconnected at one end to the fluid coupling interface 30 and may each be fluidly interconnected at another end to the thermal exchange module 40. In turn, fluid may be circulated in to and out of a first volume 41 of the thermal exchange module 40 for thermal exchange with blood that is separately flowed through a second volume 42 of the thermal exchange module 40 across a thermal exchange member 43 (e.g., a grooved/pleated metal member) of the thermal exchange module 40, wherein the first volume 41 and second volume 42 are fluidly isolated. To provide for such blood flow, system 1 may include a blood pump 70 (e.g., a peristaltic pump) for flowing blood through a first blood flow line 54 (e.g., a length of flexible tubing) fluidly interconnected to the second volume 42 of the thermal exchange module 40, the second volume 42 thermal exchange module 40, and a second blood flow line 55 (e.g., a length of flexible tubing) fluidly interconnected to the second volume 42 of the thermal exchange module 40.

As noted above, controller 10 may provide output signals for use in the operation of fluid conditioning assembly 20. More particularly, output signals 12a may include a signal for use in controlling the speed and/or duty cycle of the fluid pump 21 and a signal for controlling a cooling rate of the heat exchanger 23, and optionally, for controlling a warming rate of the heat exchanger 23. For example, the output signals 12a may include a signal for controlling a duty cycle of heat exchanger 23 and/or for controlling magnitude of thermal exchange 23 provided by heat exchanger per time unit of operation. Further, the controller 10 may optionally provide an output signal 12b for initializing and/or terminating operation of the blood pump 70.

The output signal 12b may be provided directly to the blood pump 70, or may be provided to an optional controller 18 that employs the output signal 12b to initiate/terminate operation of blood pump 70. In one arrangement, the thermal exchange module 40 and blood pump 70, and optional controller 18, may be supportably interconnected to a second support structure 200. In another arrangement, the thermal exchange module 40 and blood pump 70 may be supportably interconnected to the first support structure 100.

The output signals 12a may be provided to control thermal exchange between the circulated fluid and the blood flowed through the second volume 42 of the thermal exchange module 40 in thermal exchange module 40. For example, the rate of thermal exchange between the circulated fluid and the blood flowed through the second volume 42 of the thermal exchange module 40 may be controlled so as to achieve a desired amount of blood cooling, and optionally warming, and in turn, a desired degree of patient temperature cooling for induced hypothermia and optional patient temperature warming to achieve normothermia.

To generate the output signals 12a, the controller 10 may be provided to utilize a number of signals provided by one or more sensors comprising system 1. In particular, system 1 may include at least a first fluid temperature sensor 24 for sensing a temperature of the circulated fluid and providing a first fluid temperature signal 25 indicative thereof to controller 10. The first fluid temperature sensor 24 may be provided as part of the fluid conditioning assembly 20 and disposed to sense a temperature of the circulated fluid to be supplied through fluid coupling interface 30 to thermal exchange module 40. Additionally, in patient temperature control applications, controller 10 may be further provided to receive a patient temperature signal 82 from a patient temperature sensor 80, wherein the patient temperature signal is indicative of a sensed temperature of a patient P (e.g., a patient core temperature).

Optionally, the fluid conditioning system 20 may also include a flow meter sensor 22 for measuring a flow rate of the circulated fluid (e.g., between the pump 21 and heat exchanger 22) and providing a flow rate signal 22a indicative thereof to controller 10, and a second fluid temperature sensor (not shown in FIG. 1) for sensing a temperature of the circulated fluid returning from thermal exchange module 40 (e.g., upstream of pump 21) and providing a second fluid temperature signal indicative thereof to controller 10. The flow rate signal 26 and/or second fluid temperature signal may also be utilized by controller 10 to generate one or more of the output signals 12a.

Further, system 1 may comprise a blood temperature sensor 44 for sensing a temperature of the blood and providing a blood temperature signal 45 indicative thereof to controller 10. The blood temperature sensor 44 may be disposed within the second volume 42 of the thermal exchange module 40, or downstream of the thermal exchange module 40, to measure the temperature of the blood flowed through the second volume 42 of the thermal exchange module 40. Controller 10 may be provided to utilize the blood temperature signal 45 to control operation of the blood pump 70. For example, controller 10 may be provided to utilize blood temperature signal 45 to determine whether the sensed blood temperature is greater than a predetermined magnitude, in which case controller 10 may provide an output signal 12b to terminate operation of blood pump 70. While not shown in FIG. 1, system 1 may also include one or more blood flow pressure sensor(s) to sense the pressure of blood in thermal exchange module 70 and/or in the first and/or second blood flow lines 54 and 55, respectively, and to provide a blood pressure signal(s) indicative thereof to controller 10. In turn, controller 10 may utilize the blood pressure signal(s) to terminate operation of blood pump 70 in the event the sensed blood pressure is outside of a predetermined range.

In certain embodiments, system 1 may include a multi-lumen catheter 60 for accessing a vascular system of a patient (e.g., the femoral vein or subclavian vein of the patient). Multi-lumen catheter 60 may include a catheter portion 64 having a first port 65 and a second port 66 fluidly interconnected to a first lumen 61 and a second lumen 62, respectively, wherein the first and second lumens 61, 62 have ends (e.g., luer connectors) that may be fluidly interconnectable to first blood flow line 54 and second blood flow line 55, respectively. By way of example, first blood flow line 54 and second blood flow line 55 may be provided with complimentary members 56 and 57 (e.g., luer connectors) adapted for selective interconnection to and disconnection from the ends of the first and second lumens 61, 62, respectively, of multi-lumen catheter 60.

Upon operation of blood pump 70, blood may be drawn at negative pressure from a patient through the first port 65 and first lumen 61 of multi-lumen catheter 60, through a first portion of first blood flow line 54 upstream of blood pump 70. At blood pump 70, the blood may be pumped through a second portion of first blood flow line 54, through the second volume 42 of thermal exchange module 40, through second blood flow line 55, and through the second lumen 62 of the multi-lumen catheter 60 for return to a patient via the second port 66 of the multi-lumen catheter 60 (e.g., downstream of the first port 65). As may be appreciated, the blood may be cooled or optionally warmed as it passes through the thermal exchange module 40, wherein upon return to a patient, patient cooling or optional warming may be realized. While not shown in FIG. 1, thermal exchange module 40 may be provided with a bubble trap (e.g., an integrated 150 micron screen filter), a purge port/line with a 4-way stop cock, and a one-way valve for blood priming of the second volume 42.

In one embodiment, the multi-lumen catheter 60 may comprise a third port 67 in the catheter portion 64 that is fluidly interconnected to a third lumen 68 having an end (e.g., a luer connector) provided for selective fluid interconnection to and disconnection from an optional component 300, e.g., via an optional fluid line 58 having a complimentary member 59 (e.g., a luer connector) provided for selective interconnection to and disconnection from the end of the third lumen 68 of multi-lumen catheter 60. In one approach, optional component 300 may comprise a fluid source and fluid displacement component (e.g., a pump, syringe, etc.) for passing fluid from the fluid source through the third lumen 68 of the multi-lumen catheter 60 into a patient via third port 67. By way of example, the fluid at the fluid source may comprise one of the following:

- an anticoagulant (e.g., heparin);
- an anti-shivering agent (e.g., meperidine);
- a contrast media (e.g., a radio opaque iodine or barium compound); and
- a cooled fluid (e.g., a cooled saline solution).

In another approach, the optional component 300 may comprise a blood pressure sensor that senses a blood pressure of a patient and provides a blood pressure signal indicative thereof. The blood pressure signal may be provided to an output device to provide a blood pressure indication to a user. In some applications, the sensed blood pressure may be compared to a predetermined pressure range, e.g., at controller 10, and the output device may be adapted to provide a visual and/or audible alert output if the sensed blood pressure is outside of the predetermined pressure range.

The multi-lumen catheter 60 may be provided with the first lumen 61 and the second lumen 62 each being no more than about 12 gauge (i.e., 0.28 cm diameter). Such lumen sizing desirably accommodates laminar blood flow therethrough at blood flow rates up to at least 400 ml/min. Further, the third lumen 68 may be 17 gauge (i.e., 0.15 cm diameter). Relatedly, the multi-lumen catheter may be provided so that the catheter portion is about 13 French or less.

As noted above, a fluid coupling interface 30 may be provided for fluid interconnection to thermal exchange module 40 via first and second fluid lines 51 and 52. In that regard, the first and second fluid lines 51 and 52 may be provided with end connectors 53 (e.g., spring-loaded, quick connection fittings) adapted for selective interconnection to and disconnection from complimentary parts of fluid coupling interface 30.

Additionally, in some embodiments, the fluid coupling interface 30 may be provided for selective fluid interconnection with one or more patient contact pad(s) 90 that may be utilized for thermal exchange with a patient via contact engagement (e.g., via direct skin contact for thermal exchange across an adhesive surface of the pad(s)), as taught in one or more U.S. Pat. No. 6,669,715 to Hoglund et al.; U.S. Pat. No. 6,827,728 to Ellingboe et al.; U.S. Pat. No. 6,375,674 to Carson; and U.S. Pat. No. 6,645,232 to Carson, all of which are here by incorporated by reference in their entirety. More particularly, fluid supply line 91 and fluid return line 92 may be provided with end connectors adapted for selective interconnection to and disconnection from contact pad(s) 90 at one end and with end connectors 93 at another end (e.g., spring-loaded, quick connection fittings) for selective interconnection to and disconnection from fluid coupling interface 30.

Optionally, the fluid coupling interface 30 may include a valve 32 to provide for selective fluid coupling between fluid conditioning assembly 20 and thermal exchange module 40 or between fluid conditioning assembly 20 and contact pad(s) 90. The optional valve 32 may be provided for manual control or may be provided for automated control via a control signal 14 provided by controller 10, e.g., pursuant to user input instructions to controller 10.

Figure 2:
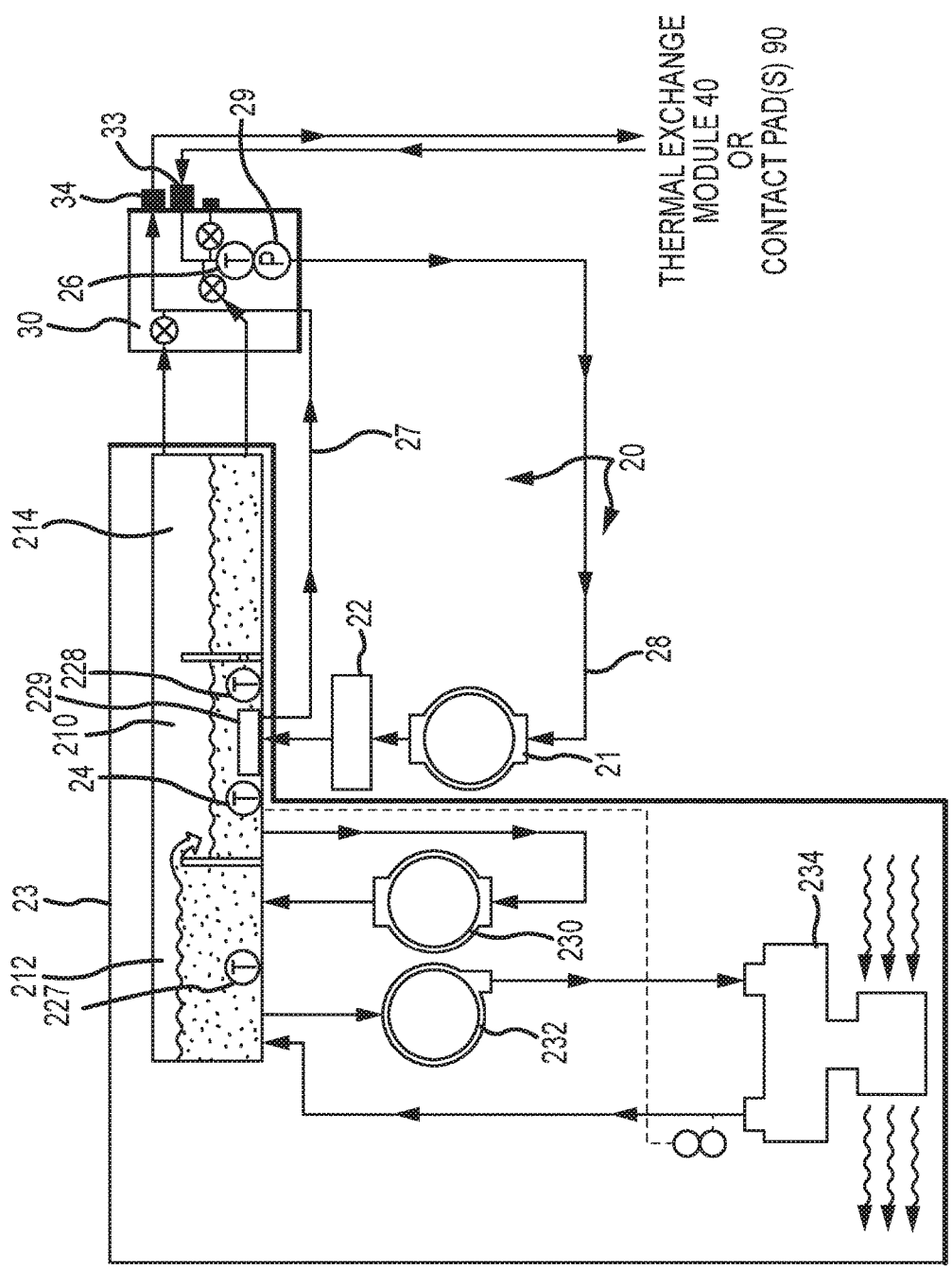
FIG. 2 is a schematic illustration of an embodiment of a fluid conditioning assembly for use in the system embodiment of FIG. 1.

FIG. 2 illustrates an embodiment of a fluid conditioning assembly 20 for use in the system embodiment of FIG. 1. As shown, fluid conditioning assembly 20 includes fluid pump 21 for pumping fluid through a flow meter 22 in to heat exchanger 23. Upon operation of fluid pump 21, fluid may be drawn from heat exchanger 23 through outlet line 27, through an outlet port 34 of fluid coupling interface 30, through the fluidly interconnected thermal exchange module 40 or contact pad(s) 90, through inlet port 33 of fluid coupling interface 30, and through inlet line 28.

Heat exchanger 23 may include a circulation tank 210 to receive the circulated fluid from fluid pump 21. In order to provide for an adequate amount of fluid, heat exchanger 23 may also optionally include a supply tank 214 for containing fluid that may flow into circulation tank 210 as needed in order to maintain a predetermined minimum amount of fluid in circulation tank 210 for flow in the described arrangement.

Heat exchanger 23 may further include a chiller tank 212 and a mixing pump 230 for pumping fluid from within circulation tank 210 into chiller tank 212. Additionally, heat exchanger 23 may include a chiller pump 232 and an evaporator/chiller 234, wherein upon operation of chiller pump 232 fluid may be pumped from chiller tank 212 through evaporator/chiller 234 and back into chiller tank 212 to yield cooling of fluid within chiller tank 212. In turn, fluid contained within chiller tank 212 may flow back into circulation tank 210 (e.g., by flowing over a barrier), wherein the fluid contained in circulation tank 210 may be cooled to a desired temperature via operation of mixing pump 230, chiller pump 232, and evaporator/chiller 234.

In that regard, operation of mixing pump 230, chiller pump 232, and evaporator/chiller 234 may be controlled by the output signals 12a of controller 10. As described above, the output signals 12a may be generated by controller 10 utilizing the first temperature signal 25 provided by first temperature sensor 24. As shown in FIG. 2 the first temperature sensor 24 may be located to sense the temperature of the fluid in circulation tank 210.

As further shown in FIG. 2, a second fluid temperature sensor 26 may be provided downstream of inlet port 33 to sense the temperature of the circulated fluid that is returned from the thermal exchange module 40 or contact pad(s) 90. The second fluid temperature sensor 28 may provide a second temperature signal to controller 10 indicative of the sensed temperature for use in generation of output signals 12a. Further, a third fluid temperature sensor 227 may be provided to sense the temperature of fluid within chiller tank 212 and provide a third temperature signal indicative of the sensed temperature. In turn, the third temperature signal may be utilized by controller 10 to generate output signals 12a. To provide redundancy in relation to the first fluid temperature sensor 24, a fourth fluid temperature sensor 228 may also be provided within circulation tank 210 to provide a fourth temperature signal indicative of the sensed temperature for redundant potential usage by controller 10 in generating output signals 12a.

In the arrangement illustrated in FIG. 2, a fluid pressure sensor 29 may also be provided to sense the pressure of the circulated fluid returning from thermal exchange module 40 or contact pad(s) 90. In turn, the pressure sensor 29 may provide a pressure signal to controller 10 indicative of the sensed pressure. In turn, controller 10 may utilize the pressure signal to generate output signals 12a provided to fluid pump 21, e.g., to control the speed of fluid pump 21 to provide for desired negative pressure within the second volume of thermal exchange module 40 or within contact pad(s) 90.

With further reference to FIG. 2, heat exchanger 23 may include a heater 229 for selective heating of the fluid contained in circulation tank 210. In that regard, heater 229 may be provided to receive output signals 12a from controller 10 to provide a desired degree of heating to the fluid in circulation tank 210. As may be appreciated, operation of heater 229 may be utilized to heat the circulated fluid so as to effect patient rewarming in various embodiments.

Figure 3:
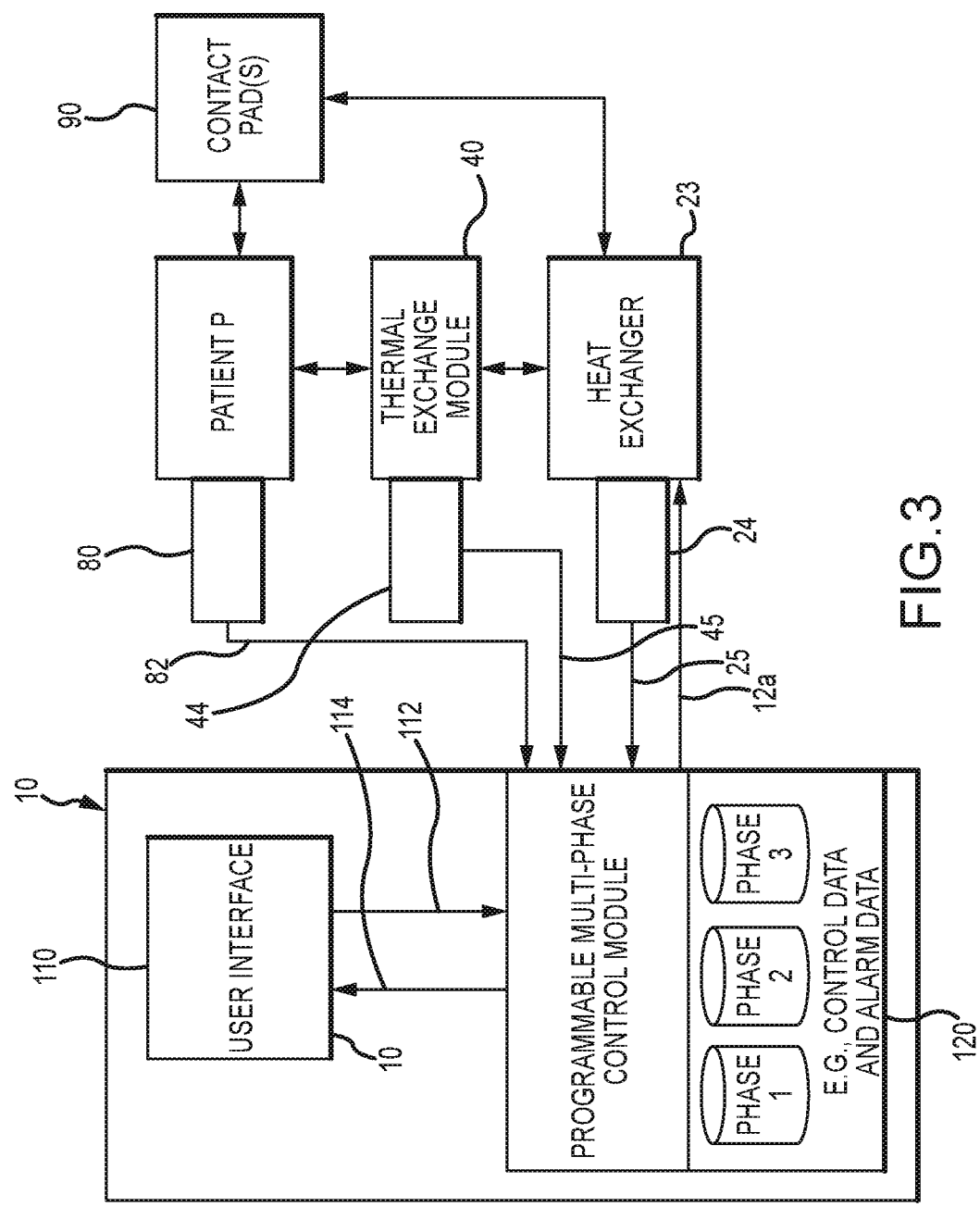
FIG. 3 is a schematic illustration of a controller embodiment for use in the system embodiment of FIG. 1.

FIG. 3 illustrates one embodiment of a controller 10. The controller 10 may be computer-based (e.g., a microprocessor) and may include a programmable control module 120 and a user interface 110 for receiving user control input and for providing corresponding signals 112 to the programmable control module 120. User interface 110 may be further adapted to receive signals 114 from the programmable control module 120 for use in the display of control and measured data and for operative, interactive interface with a user at user interface 110.

The programmable control module 120 may be provided to store control data (e.g., via a computer readable medium) and generate signals in corresponding relation to a plurality of different temperature control phases. In that regard, the programmable control module may comprise control logic for utilizing the control data to provide output signals to the heat exchanger 23 and/or the fluid pump 21 and/or the blood pump 70, wherein the temperature of the circulated fluid is controlled in a predetermined manner for each of the plurality of different temperature control phases. Additionally or alternatively, the programmable control module 120 may be provided to facilitate the establishment of one or more programmed protocols that each comprise control data for use in the control of each of the plurality of temperature control phases. By way of example, a given protocol may comprise control data that includes target patient temperature data for each of a plurality of treatment phases. Further, for one or more of the phases, the protocol may comprise control data comprising a set duration for thermal treatment. As may be appreciated, the user interface 110 may be adapted for use in receiving user input to establish the control data corresponding with each of the plurality of different patient temperature control phases on a protocol-specific basis.

For each given protocol the programmable control module 120 may provide output signals 12a to at least the heat exchanger 23, and optionally to fluid pump 21 and blood pump 70, on a phase-specific basis. In turn, thermal exchanger 23 may be provided to responsively change the temperature of the circulated fluid to affect a desired thermal exchange with a patient, e.g., to cool, maintain the temperature of, or warm the blood flowed through the thermal exchange module 40, and in turn, the patient P, and/or to cool, maintain the temperature of, or warm a patient via contact thermal exchange via contact pad(s) 90. For example, and as noted above, heat exchanger 23 may comprise various componentry which operate to change the temperature of the circulated fluid in corresponding relation to control signals 12a output from the programmable control module 120.

Optionally, the system may be provided for multi-mode operation. In one mode, the programmable control module 120 may be provided for cooling/heating and circulating fluid water through thermal exchange module 40 for thermal exchange with blood circulated therethrough, e.g., for vascular thermal exchange with patient P. In another mode, the programmable control module 120 may be provided for cooling/heating and circulating fluid through one or a plurality of fluidly interconnected pads 90 designed for intimate contact with and thermal energy exchange with patient P.

As discussed above, system 1 may comprise a first fluid temperature sensor 24 for sensing the temperature of the circulated fluid on an ongoing basis and providing a corresponding first fluid temperature signal 25 to the controller 10. Further, patient temperature sensor 80 may be provided to sense the temperature of the blood or patient P on an ongoing basis and provide corresponding signal 82 to the controller 10. In turn, the signals 25 and 82 may be employed by the programmable control module 120, together with control data and preset algorithms, to generate (e.g., via the processor logic) the control signals 12a provided to heat exchanger 23, so as to yield the desired temperature of the circulated fluid (e.g., on a single phase or phase specific basis).

In one approach, the control data for a first phase of the plurality of different control phases may be established so that, during the first phase, the circulated fluid may be cooled to cool the blood circulated through the thermal exchange module 40 so that the patient reaches an established target patient temperature (e.g., corresponding with induced hypothermia). For such purposes, the controller 10 may utilize a patient temperature signal 82 as referenced above to determine whether or not and when a patient has reached the established target patient temperature (e.g., by comparison of the corresponding patient temperature to the established target patient temperature) and to provide output signals 12a to the heat exchanger 23 and/or fluid pump 21 responsive thereto. In one implementation, the circulated fluid may be cooled at a predetermined rate (e.g., a predetermined maximum rate) to cool a patient to the established target patient temperature as rapidly as possible (e.g., within predetermined system limits).

Optionally, the control data for the first phase of the plurality of different control phases may further comprise an established duration measure, wherein once the established target patient temperature is reached the patient is maintained at the established target patient temperature for any remaining portion of the established duration measure. Alternatively, the control data for a second phase of the plurality of different control phases may be established so that, during the second phase, the circulated fluid may be maintained at a temperature so that, via thermal exchange with the blood circulated through the thermal exchange module, the patient is maintained at the established target patient temperature for an established duration of the second phase. Again, for such purposes, the controller 10 may utilize a patient temperature signal 82, as referenced above (e.g., to compare the corresponding patient temperature to the established target patient temperature) and to provide output signals 12a to the heat exchanger 23 and/or fluid pump 21 responsive thereto.

In further conjunction with the described approach, the control data for an additional phase after the first phase (e.g., a second phase or a third phase of the plurality of different control phases) may be established so that, during such phase, the circulated fluid may be warmed (e.g., at a predetermined rate) to warm the blood circulated through the thermal exchange module 40 so that the patient reaches another established target patient temperature (e.g., corresponding with normothermia), and optionally, so that once such another established target patient temperature is reached, the patient is maintained at the another established target patient temperature for any remaining balance of an established duration of the additional phase or until the thermotherapy procedure is manually terminated by a user. For such purposes, the controller 10 may again utilize a patient temperature signal 82, as referenced above (e.g., to compare the corresponding patient temperature to the another established target patient temperature), and to provide output signals 12a to the heat exchanger 23 and/or fluid pump 21 responsive thereto.

As noted, the controller may comprise a user interface 110 for receiving user input and providing user control signals, wherein the control logic of the programmable processor control module 110 utilizes the user control signals together with the control data to provide the output signals 12a. The user interface 110 may be further provided to establish and modify the control data stored by the programmable control module.

In some arrangements, the programmable control module may be operable to store at least two protocols comprising corresponding, different control data. In turn, the user interface 110 may be employable by user to select either of the two protocols for use by the programmable control module in generating the output signals.

Optionally, the user interface 110 may be provided to include a graphic display to visually present a plot of a target patient temperature adjustment rate that is based on the stored control data for a plurality of different temperature control phases. Further, the graphic display may be operable to display a plot of a sensed patient temperature (e.g., as sensed by the patient temperature sensor) in corresponding time relation to the plot of the target patient temperature adjustment rate. Further, the graphic display may be operable to display a plot of a sensed temperature of the circulated fluid (as sensed by the first fluid temperature sensor) and a sensed temperature of the blood flowed through the second volume of the thermal exchange module (as sensed by the blood temperature sensor) in corresponding time relation to the plot of the target patient temperature adjustment rate.

In relation to one example of system 1, the fluid conditioning assembly 20 may utilize the Arctic Sun 5000 Temperature Management System product of Medivance, Inc., located in Louisville, Colo., USA. Further, the patient contact pad(s) 90 may comprise the Arctic Gel pad product of Medivance, Inc., located in Louisville, Colo., USA. Additionally, the multi-lumen catheter 60 may comprise the Power Trialysis catheter product of Bard Access Systems, Inc., located in Salt Lake City, Utah. Additionally, the thermal exchange module 40 may comprise the CSC14 Cardioplegia Heat Exchanger product of Soren Group Italia S.r.I., located in Mirendola, Italy.

Figure 4:
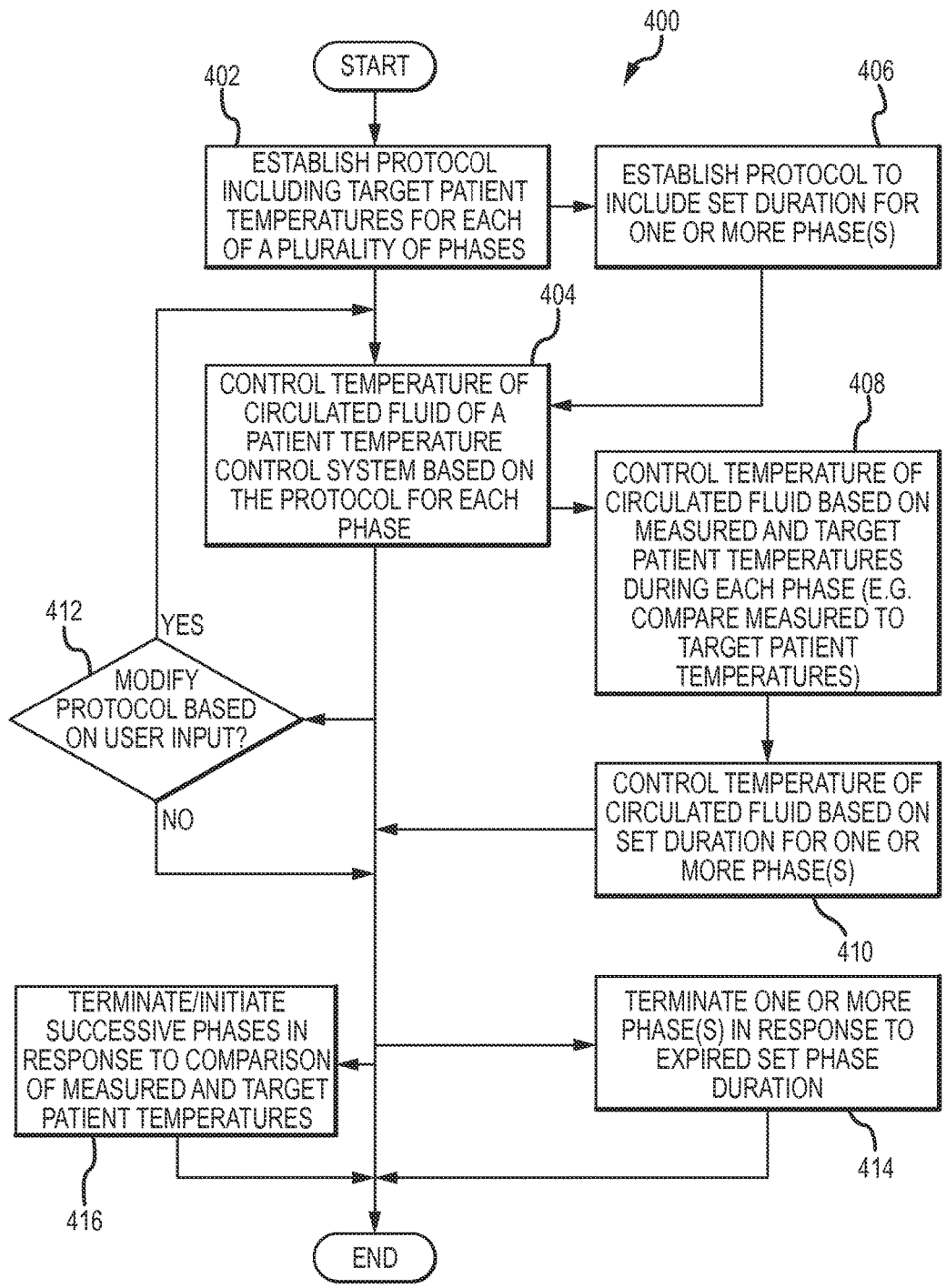
FIG. 4 illustrates one embodiment of a method for extracorporeal blood temperature control and patient temperature control.

FIG. 4 illustrates one embodiment of a method 400 for controlling the temperature of a patient via control of the temperature of the circulated fluid in a multi-phase temperature control system. As illustrated, the method 400 may include an initial step 102 of establishing a protocol that includes target patient temperatures for a plurality of different temperature control phases (e.g., two or more non-overlapping phases having different patient temperature exchange objectives). Such phases may be successive in time and/or spaced in time. The establishment of a protocol may be achieved via use of the programmable control module 120 and operatively interconnected user interface 110 of FIG. 3.

By way of example, the protocol may be established to include target patient temperatures for at least three phases. Such an approach facilitates a procedure in which a patient is cooled to a first target patient temperature in a first phase of therapy, maintained at or within a predetermined range of a second target patient temperature during a second phase (e.g., equal or different than the first target temperature), and warmed to a third target patient temperature during a third phase. In other embodiments, following a third phase of therapy it may be desirable to establish a fourth target patient temperature for use in temperature control during a fourth phase of therapy.

The method may further include a step 404 of controlling the temperature of the circulated fluid based on the protocol for each of the plurality of phases, e.g., via control of the heat exchanger 23 via output signals 12a to control the temperature of the circulated fluid of FIGS. 1 and 2. In that regard, the protocol may be further established at step 406 so as to include a set duration for one or more of the phases, e.g., via use of a programmable control module 120 and user interface 110 of FIG. 3. In turn, the controlling step 404 may be carried out during such phase(s) for a duration(s) that corresponds with the set duration.

In one approach, the controlling step 404 may be carried out in step 408 for each phase by controlling the temperature of the circulated fluid based upon a sensed patient temperature and the target patient temperature for such phase, e.g., via use of a patient temperature signal 82 from patient temperature sensor 80 by the programmable control module 120 of FIG. 1. By way of example, the patient temperature may be sensed on an ongoing basis during a given phase and compared to the corresponding target patient temperature for such phase. Based upon such comparison, system 1 may provide for cooling and/or heating of the circulated fluid according to any of a plurality of pre-established algorithms, e.g., via control of the heat exchanger 23 by the programmable multi-phase control module 120 of controller 10 of FIG. 3.

In one approach, a control algorithm may provide for simply turning on/off the cooling/heating componentry of the heat exchanger 23 of system 1 (e.g., evaporator/chiller 234, chiller pump 232, and mixing pump for fluid cooling, and heater 229 for fluid heating) in intervals that depend upon a degree of difference reflected by comparison of the sensed patient temperature and target patient temperature. In another approach, a control algorithm may provide for controlling an output magnitude of the cooling/heating componentry of the heat exchanger 23 of system 1 (e.g., evaporator/chiller 234, chiller pump 232, and mixing pump for fluid cooling, and heater 229 for fluid heating) based upon a degree of difference reflected by comparison of the measured patient temperature and target patient temperature.

In another approach, the controlling step 404 may be completed as step 410 for a given phase by controlling the temperature of a thermal exchange medium based upon a sensed patient temperature, an established target patient temperature for such phase, and an established set duration for such phase. For example, utilization of the noted parameters accommodates the determination and control use of a target patient temperature adjustment rate for the phase, wherein gradual patient cooling/warming over a desired time period may be facilitated.

In yet another approach, one or more sensed circulated fluid temperature(s) (e.g., as sensed by first temperature sensor 24 and optionally second temperature sensor 26) may be employed together with a sensed patient temperature (e.g., as sensed by patient temperature sensor 80) and established target patient temperature (e.g., comprising control data stored at programmable control module 110) to control the heating/cooling of the circulated fluid. Such an approach may yield enhanced system response.

The illustrated method 400 may further provide for modification of a given protocol based on user input at step 412, e.g., via user input at the user interface 110 of FIG. 3. In this regard, a modified protocol may be employed for the remaining duration of a modified phase(s) and for any phase(s) that have not yet been initiated.

In the illustrated method, a given phase may be automatically terminated at step 414 by expiration of a corresponding set duration included within the programmed protocol for such phase. In that regard, the termination of a given phase may generally correspond with a change in the mode (e.g., cooling or heating) or a change in the magnitude of thermal exchange between the circulated fluid and a patient.

Method 400 may also provide for the termination and initiation of successive phases at step 416 in response to a comparison of a sensed patient temperature and a target patient temperature. That is, upon determining that a target patient temperature has been reached during a given phase (e.g., via comparison of a sensed patient temperature and a target patient temperature for an initial phase of treatment), such phase may be automatically terminated and a successive phase automatically initiated. Alternatively and/or additionally, the method 400 may also provide for the termination and initiation of successive phases in response to the expiration of a set duration for a first one of the two successive phases. The automatic phase termination/initiation features may be selectively established by a user for a given protocol on a phase-specific basis.

In relation to method 400, in one embodiment the plurality of different temperature control phases may be completed in a first mode of operation in which fluid and blood are circulated through a thermal exchange module 40, as described above, to provide vascular patient cooling and optional warming. In another embodiment, a portion or all of at least one of the plurality of different temperature control phases is completed in the first mode of operation during a first time period, and another portion or all of another one of the plurality of different temperature control phases is completed in a second mode of operation during a second time period (e.g., after the first time period) in which fluid is circulated through one or more patient contact pad(s) 90, as described above, to provide contact patient cooling and optional warming.

In one approach, the first mode of operation (i.e., during which circulated fluid and blood are circulated through the thermal exchange module 40) may be employed to complete all or at least a portion of a first phase of the plurality of different temperature control phases. For example, in the first phase, the blood circulated through the thermal exchange module 40 may be rapidly cooled to cool the patient to an established target patient temperature (e.g., comprising first phase control data and corresponding with induced hypothermia). Then, during a remaining portion of the first phase or during a second phase during which the patient may be maintained at the established target patient temperature for an established duration (e.g., comprising second phase control data), the second mode of operation may be employed. Further, in an additional phase after the first phase (e.g., a second phase or a third phase) during which the patient may be warmed (e.g., at a predetermined rate) to warm the patient to another established target patient temperature (e.g., comprising corresponding phase control data and corresponding with normothermia) and optionally maintained at such temperature for any remaining balance of an established duration (e.g., comprising corresponding phase control data) or until the thermotherapy procedure is manually terminated, the second mode of operation may be employed.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A system for extracorporeal blood temperature control, comprising:
   a heat exchanger for at least cooling a fluid, wherein the heat exchanger includes a circulation tank for containing the fluid;
   a thermal exchange module having a first volume and a second volume fluidly isolated from one another;
   a fluid pump fluidly interconnected to the circulation tank of the heat exchanger to circulate said fluid through said circulation tank of said heat exchanger, and fluidly interconnected to the first volume of the thermal exchange module to circulate the fluid through the first volume of the thermal exchange module, wherein operation of said fluid pump establishes a negative pressure within the first volume of said thermal exchange module so that said fluid is drawn from the circulation tank through the first volume of said thermal exchange module;
   a blood pump for flowing blood through a first blood flow line, said second volume of said thermal exchange module, and a second blood flow line; and,
   a first controller for providing output signals for use in operation of at least said heat exchanger to selectively control at least cooling of the fluid contained in the circulation tank to a desired temperature for thermal exchange between said fluid circulated through the first volume of the thermal exchange module and said blood flowed through the second volume of the thermal exchange module and thereby provide for at least selective cooling of the circulated blood.

2. The system of claim 1, wherein the circulation tank is separately fluidly interconnected to an outlet port of the fluid pump and an inlet port of the first volume of the thermal exchange module, and wherein an outlet port of the thermal exchange module is fluidly interconnected to an inlet port of the fluid pump.

3. The system of claim 1, further comprising:
   a first fluid temperature sensor for sensing a temperature of said circulated fluid and providing a first fluid temperature signal indicative thereof, wherein said first controller is provided to utilize said first fluid temperature signal to generate said output signals.

4. The system of claim 3, further comprising:
   a blood temperature sensor for sensing a temperature of said blood flowed through the second volume of the thermal exchange module and providing a blood temperature signal indicative thereof, wherein the first controller is provided to utilize said blood temperature signal to provide an output signal for use in operation of the blood pump.

5. The system of claim 3, wherein said first controller is further provided to receive a patient temperature signal indicative of a sensed patient temperature, and to utilize the patient temperature signal together with said first fluid temperature signal to generate said output signals.

6. The system of claim 1, further comprising:
a multi lumen catheter fluidly interconnectable or interconnected to said first and second blood flow lines to receive said blood flowed through the second volume of the thermal exchange module from and return said blood flowed through the second volume of the thermal exchange module to a patient vascular system.

7. The system of claim 6, wherein said multi lumen catheter comprises:
a catheter portion having at least a first port and a second port;
a first lumen, fluidly interconnected to said first port, having an end fluidly interconnectable or interconnected to said first blood flow line; and,
a second lumen, fluidly interconnected to said second port, having an end fluidly interconnectable or interconnected to said second blood flow line.

8. The system of claim 7, wherein said catheter portion of said multi lumen catheter further comprises a third port, and said multi lumen catheter further comprises:
a third lumen, fluidly interconnected to said third port, having an end selectively, fluidly interconnectable to an optional component, wherein said optional component comprises a fluid source of a fluid that comprises:
an anticoagulant;
an anti-shivering agent;
a contrast media; or
a cooled fluid.

9. The system of claim 6, wherein the blood pump, the first and second blood flow lines, and the multi lumen catheter are provided to provide for blood flow through the second volume of the thermal exchange module at a blood flow rate within a range of about 50 ml/min to about 300 ml/min.

10. The system of claim 9, wherein the system is provided to circulate fluid through the first volume of the thermal exchange module at a rate that is at least about 5 times greater than the blood flow rate through the second volume of the thermal exchange module.

11. The system of claim 9, wherein the thermal exchange module is provided a heat exchange performance factor N>0.8 across a blood flow rate range of about 50 ml/min to about 300 ml/min, wherein:
$N=(T\_bo-T\_bi)/(T\_cfi-T\_bi)$; and,
$T\_bo$=temperature of blood flowing out of thermal exchange module;
$T\_bi$=temperature of blood flowing in to thermal exchange module; and,
$T\_cfi$=temperature of circulated fluid flowing in to thermal exchange module.

12. The system of claim 1, wherein said controller further comprises:

a programmable processor control module for storing control data in relation to a plurality of different temperature control phases during which a temperature of the circulated fluid is controlled differently, wherein said programmable control module comprises control logic for utilizing said control data to provide said output signals.

13. The system of claim 12, wherein said heat exchanger is further provided for heating said circulated fluid contained in the circulation tank, and wherein said control data comprises:
cooling control data for use by said control logic in providing said output signals to said heat exchanger to provide for said cooling of said blood in at least one of said plurality of temperature control phases; and,
warming control data for use by said control logic to said heat exchanger in providing said output signals to said heat exchanger to provide for said warming of said blood in at least another of said plurality of temperature control phases.

14. The system of claim 12, further comprising:
a user interface for receiving user input and providing user control signals, wherein said control logic utilizes said user control signals together with said control data to provide said output signals, and wherein said user interface is employable to modify said control data stored by said programmable control module.

15. The system of claim 14, wherein said user interface includes:
a graphic display to visually present a plot of a target patient temperature adjustment rate based on said stored control data, and a plot of a sensed patient temperature in corresponding time relation to said plot of said target patient temperature adjustment rate.

16. The system of claim 15, wherein said graphic display is operable to display a plot of a sensed temperature of said circulated fluid and a sensed temperature of said blood flowed through the second volume of the thermal exchange module in corresponding time relation to said plot of said target patient temperature adjustment rate.

17. The system of claim 12, wherein said programmable control module is operable to store at least two protocols comprising corresponding, different control data, and wherein said user interface is employable by a user to select either of said two protocols for use by said programmable control module in generating said user control signals.

18. The system of claim 12, wherein said control data for a first phase of said plurality of different temperature control phases comprises at least one of a target patient temperature and a target blood temperature; and
wherein said control data for a second phase of said plurality of different temperature control phases comprises a duration measure and at least one of a target patient temperature and a target blood temperature.

19. The system of claim 18, wherein said control data for said first phase of said plurality of different temperature control phases further comprises a duration measure.

20. The system of claim 18, wherein said control data for a third phase of said plurality of different temperature control phases comprises at least one of a target patient temperature and a target blood temperature.

* * * * *